US005565362A

United States Patent [19]
Rosen

[11] Patent Number: 5,565,362
[45] Date of Patent: Oct. 15, 1996

[54] DNA SEQUENCES TO TARGET PROTEINS TO THE MAMMARY GLAND FOR EFFICIENT SECRETION

[75] Inventor: Jeffrey M. Rosen, Houston, Tex.

[73] Assignee: Pharming B.V., Leiden, Netherlands

[21] Appl. No.: 185,574

[22] Filed: Jan. 24, 1994

Related U.S. Application Data

[63] Continuation of Ser. No. 602,066, Oct. 24, 1990, Pat. No. 5,304,489, which is a continuation of Ser. No. 14,952, Feb. 17, 1987, abandoned.

[51] Int. Cl.$^6$ .......................... C12N 15/00; C07H 21/00
[52] U.S. Cl. .................... 435/320.1; 435/172.3; 435/69.1; 800/2; 800/DIG. 1
[58] Field of Search .................. 435/320.1, 172.3, 43569.1, 317.1; 800/2, DIG. 1; 536/23.1; 935/111

[56] References Cited

U.S. PATENT DOCUMENTS 4,873,316  10/1989  Meade et al. .

FOREIGN PATENT DOCUMENTS

| 0264166 | 4/1988 | European Pat. Off. . |
| WO88/00239 | 1/1988 | WIPO . |
| WO88/01648 | 3/1988 | WIPO . |

OTHER PUBLICATIONS

Wilmut et al., "A Revolution in Animal Breeding," *New Scientist*, Jul. 7, 1988, pp. 56–59.

Van Brunt, "Molecular Farming: Transgenetic Animals as Bioreactors," *Biotechnology*, 6(10):1149–1154 (1988).

Lee et al., "Expression of the Rat Beta–Casein Gene in Transgentic Mice," *J. Cell. Biology–Twenty–Sixth Annual Meeting of the American Society for Cell Biology*, 103(5 part 2):313A, Abstract No. 1161 (Dec. 1986).

Bisbee et al., "DNA Sequence Elements Regulating Casein Gene Expression," *Transcription Control Mechanisms–UCLA Symposium on Molecular and Cellular Biology*, Apr. 6–13, 1986, 52:313–323.

Clark et al., "Pharmaceuticals from Transgenic Livestock," *Trends in Biotechnology*, 5(1):20–24 (Jan. 1987), Elsevier Science Publishers, B.V. Amsterdam, NL.

Lathe et al., "Novel Products from Livestock," (Proceedings of a Seminar in the CEC Animal Husbandry Research Programme; Edinburgh, UK, 19–20 Jun., 1985) in *Exploiting New Technologies in Animal Breeding: Genetic Developments* (C. Smith et al. eds., Oxford University Press, 1986) p. 91–102.

Mercier, "Genetic Engineering Applied to Milk Producing Animals: Some Expectations," (Proceedings of a Seminar in the CEC Animal Husbandry Research Programme; Edinburgh, UK, 19–20 Jun., 1985) in *Exploiting New Technologies in Animal Breeding: Genetic Developments* (C. Smith et al. eds., Oxford University Press, 1986) pp. 122–131.

Andres et al., "Ha–ras Oncogene Expression Directed by a Milk Protein Gene Promoter: Tissue Specificity, Hormonal Regulation, and Tumor Induction in Transgenic Mice," *Proc. Natl. Acad. Sci.* 84:1299–1303 (1987).

Schoenberger et al., "Targeted c–myc Gene Expression in Mammary Glands of Transgenic Mice Induces Mammary Tumours with Constitutive Milk Protein Gene Transcription," *The EMBO J.*, 7(1):169–175 (1988).

Pittius et al., "A Milk Protein Gene Promoter Directs the Expression of Human Tissue Plasminogen Activator cDNA to the Mammary Gland in Transgenic Mice," *Proc. Acad. Sci. USA*, 85:5874–5878 (1988).

Chandler et al., "DNA Sequences Bound Specifically by Glucocorticoid Receptor In Vitro Render a Heterologous Promoter Hormone Responsive In Vivo," *Cell*, 33:489–499, Jun. 1983.

Yu–Lee et al., "Evolution of the Caesin Multigene Family: Conserved Sequences in the 5' Flanking and Exon Region," *Nucleic Acids Research*, 14:1833–1902 (1986).

Gordon et al., "Production of Human Tissue Plasminogen Activator in Transgenic Mouse Milk," *Biotechnology*, 5:1183–1187 (1987).

Hammer et al., "Production of Transgenic Rabbits, Sheep and Pigs by Micorinjection," *Nature* 315:680–683 (1985).

Gordon et al., "Genetic Transformation of Mouse Embryos by Microinjection of Purified DNA," *Proc. Natl. Acad. Sci. USA*, 77:7380–7384 (1980).

Palmiter et al., "Transgenic Mice," *Cell*, 41:343–345 (1985).

Palmiter et al., "Germ–Line Transformation of Mice," *Annu. Rev. Genet.*, 20:465–499 (1986).

Swift et al., "Tissue–Specific Expression of the Rat Pancreatic Elastase I Gene in Transgenic Mice," *Cell*, 38:639–646 (1984).

Storb et al., "High Expression of Cloned Immunoglobulin Kappa Gene in Transgenic Mice is Restrictedto B Lymphocytes," *Nature* (London), 310:238–241 (1984).

Grosschedl et al., "Stable Propagation of the Active Transcriptional State of an Immunoglobulin Mu Gene Requires Continuous Enhancer Function," *Cell*, 41:885–897 (1984).

Shani, "Tissue–Specific Expression of Rat Myosin Light––Chain 2 Gene in Transgenic Mice," *Nature*, 314:283–286 (1985).

Chada et al., "Specific Expression of a Foreign Beta–Globin Gene in Erythroid Cells of Transgenic Mice," *Nature*, (London), 314: 377–380 (1985).

Stewart et al., "Nucleotide Sequences of Bovine Alpha S1–and Kappa–Casein cDNAs," *Nucl. Acids Res.*, 12:3895–3907 (1984).

Magram et al., "Developmental Regulation of a Cloned Adult Beta–Globin in Transgenic Mice," *Nature*, (London), 315:338–340 (1985).

Ornitz et al., "Specific Expression of an Elastase–Human Growth Hormone Fusion Gene in Pancreatic Acinar Cells of Transgenic Mice," *Nature*, (London), 313:600–602 (1985).

Krumlauf et al., "Developmental Regulation of Alpha–Fetoprotein Genes in Transgenic Mice," *Mol. Cell. Biol.*, 5:1639–1648 (1985).

Overbeek et al., "Lens–Specific Expression and Developmental Regulation of the Bacterial Chloramphenicol Acetyltransferase Gene Driven by the Murine Alpha A–Crystallin Promoter in Transgenic Mice," *Natl. Acad. Sci. USA*, 82:7815–7819 (1985).

Hanahan, "Heritable Formation of Pancreatic Beta–Cell Tumours in Transgenic Mice Expressing Recombinant Insulin/Simian Virus 40 Oncogenes," *Nature*, (London), 315:115–121 (1985).

Edlund et al., "Cell–Specified Expression of the Rat Insulin Gene: Evidence for Role of Two Distinct 5' Flanking Element," *Science*, 230:912–916 (1985).

Jones et al., "The Rat Casein Multigene Family. Fine Structure and Evolution of the Beta–Casein Gene," *J. Biol. Chem.*, 260:7042–7050 (1985).

Godowski et al., "Glucocorticoid Receptor Mutants that are Constitutive Activators of Transcriptional Enhancement," *Nature*, 325:365–368.

Maniatis et al., "Molecular Cloning: A Laboratory Manual," *Cold Spring Harbor Press*, pp. 207–209 (1982).

Gorman et al., "Recombinant Genomes Which Express Chloramphenicol Acetyltransferase in Mammalian Cells," *Mol. Cell. Biol.*, 2:1044–1051 (1982).

Kelly, "Pathways of Protein Secretion in Eukaryotes," *Science*, 230:25–32 (1985).

Rosen et al., "Membrane Receptors and Cellular Regulation," New York, pp. 385–396 (1985).

Quinn, "Preservation of Hamster Oocytes to Assay the Fertilizing Capacity of Human Spermatozoa," *J. Reprod. Fert.*, 66:161–168 (1982).

Brinster et al., "Factors Affecting the Efficiency of Introducing Foreign DNA into Mice by Microinjecting Eggs," *Proc. Natl. Sci. USA*, 82:4438–4442 (1985).

Labarca et al., "A Simple, Rapid, and Sensitive DNA Assay Procedure," *Anal. Biochem.*, 102:344–352 (1980).

Kafatos et al., "Determination of Nucleic Acid Sequence Homologies and Relative Concentration by a Dot Hybridization Procedure," *Nucl. Acid Res.*, 7:1541–1552.

Chirgwin et al., "Isolation of Biologically Active Ribonucleic Acid from Sources Enriched in Ribonuclease," *Biochem.*, 18:5294–5299.

Zinn et al., "Identification of two Distinct Regulatory Regions Adjacent to the Human Beta–Interferon Gene," *Cell*, 34:865–879 (1983).

Rosen et al., "Multihormonal Regulation of Milk Protein Gene Expression," *Ann. N.Y. Acad. Sci.*, 478:63–76 (1986).

Lee et al., "Interaction of Mouse Mammary Epithelial Cells with Collagen Substrata: Regulation of Casein Gene Expression and Secretion," *Proc. Natl. Acad. Sci. USA*, 82:1419–1423 (1985).

Levine et al. "Cell—Cell Interactions Promote Mammary Epithelial Cell Differentiation," *J. Cell. Biol.*, 100:1415–1422 (1985).

Hobbs et al., "Complex Hormonal Regulation of Rat Casein Gene Expression," *J. Biol. Chem.*, 257:3598–3605 (1982).

Church, "Embryo Manipulation and Gene Transfer in Domestic Animals," *TibTech*, 5:13–19 (1987).

Cartwright, "Isolation and Purification of Products from Aminal Cells," *TibTech*, 5:25–30 (1987).

Hammer et al., "Diversity of Alpha–Fetoprotein Gene Expression in Mice is Generated by a Combination of Separate Enhancer Elements," *Science*, 235:53–58 (1987).

Lee et al., "Cell Biology," *J. Cell Biol.*, 103, 313a, Abstract #1161 (1986).

Ross et al., "Glucocorticoid Regulation of Mouse Mammary Tumor Virus Sequences in Transgenic Mice," *Proc. Natl. Acad. Sci. USA*, 82:5880–5884 (1985).

Kraemer et al., "Gene Transfer into Pronuclei of Cattle and Sheep Zygotes," In: Genetic Manipulation of the Early Mammalain Embryo, Banbury Report #20, Cold Spring Harbor Laboratory, pp. 221–227 (1985).

Rosen et al., "Multihormonal Regulation of Milk Protein Gene Expression," *J. Cell. Biochem.*, Supp. 10D, p. 146, Abstract #0193 (1986).

Campbell & Rosen, "Comparison of the Whey Acidic Protein the Rat and Mouse," *Nucleic Acid Res.* 12:8685–97 (1984).

Khillan et al., "Developmental and Tissue–Specific Expression Directed by the $\alpha_2$ Type I Collagen Promoter in Transgenic Mice," *Proc. Natl. Acad. Sci. (USA)* 83:725–729 (1986).

*Primary Examiner*—Jasemine C. Chambers
*Attorney, Agent, or Firm*—Townsend and Townsend and Crew LLP

[57] ABSTRACT

Described is a method of targeting specific genes to the mammary gland which results in the efficient synthesis and secretion of biologically important molecules. Further, there is described as a composition of matter, a transgenic mammal having the ability to reproduce itself and being suitable for the secretion of biologically active agents into its milk. Additionally there is disclosed as a composition of matter, recombinant DNA gene complexes designed to integrate into a mammalian genome and to synthesize and secrete biological active agents into the milk. Furthermore methods of producing and using altered milk are disclosed.

18 Claims, 4 Drawing Sheets

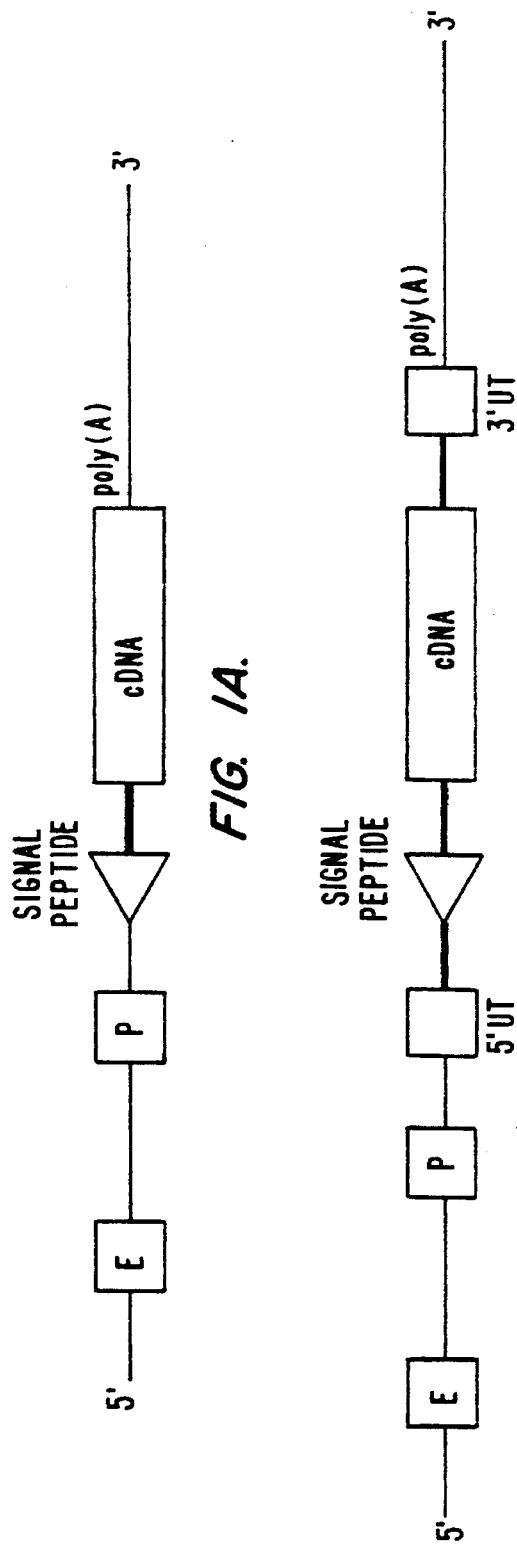

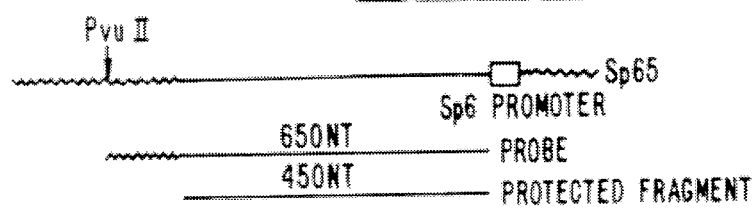
FIG. 7.
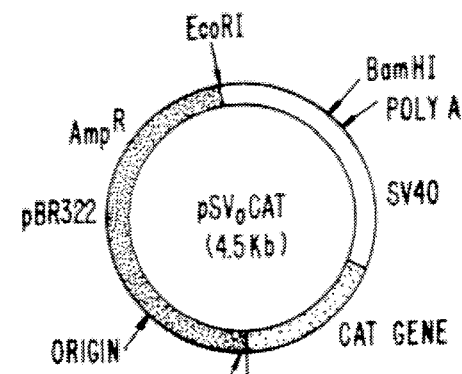
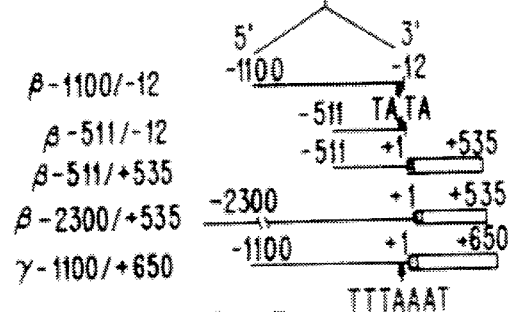
FIG. 8.

DNA SEQUENCES TO TARGET PROTEINS TO THE MAMMARY GLAND FOR EFFICIENT SECRETION

This is a continuation of application Ser. No. 07/602,066, filed Oct. 24, 1990, now U.S. Pat. No. 5,304,489, which is a continuation of Ser. No. 07/014,952, filed Feb. 17, 1987, now abandoned.

FIELD OF THE INVENTION

The present invention relates generally to transgenic mammals which secrete foreign compounds in their milk and to the method of producing transgenic mammals with altered milk containing compounds useful in the areas of pharmacology, medicine, food and agricultural production and cancer research.

BACKGROUND OF THE INVENTION

Caseins are the principal milk proteins and are normally synthesized and secreted only in the mammary gland during lactation. The first detailed characterization of the casein genes was done is the inventor's laboratory. Yu-Lee, et al., Nuc. Acids Res., 14:1833–1902 (1986)

Since its introduction, microinjection of DNA into the pronucleus of a fertilized one-cell embryo has been used to transfer a large number of genes into the mouse genome. Gordon et al. Proc. Natl. Acad. Sci. USA 77:7380–7384 (1980); Palmiter and Brinster, Cell 41:343–345 (1985) and Palmiter and Brinster Ann. Rev. Genet. 20 465–499 (1986). The technique is useful for studies of the specific nucleotide sequences involved in gene expression and regulation, and for its practical applications for improvement of domestic livestock. Transgenic sheep and pigs have now been produced. Hammer et al., Nature (London) 315:343–345 (1985). Studies in cattle are in progress. Kraemer et al., In: Gene Transfer in Cattle and Sheep, Banbury Report No. 20 pp. 221–227 (1985).

To produce transgenic animals of practical use in agriculture, the foreign gene must be integrated into the genome of the host animal and transmitted to its offspring; it must be expressed in the appropriate tissue; and its expression must be at a high rate and subject to normal or artificial regulatory mechanisms. Tissue specificity of transgene expression has been reported for several genes including the rat elastase I gene, Ig light and heavy chain genes, the rat myosin light chain gene and mouse/human $\beta$-globin gene; Swift et al., Cell 38:639–646 (1984); Storb et al., Nature (London) 310:238–241 (1984), Grosscheldl et al., Cell 41:885–897 (1984); Shani, Nature (London) 314:283–286 (1985); and Chada, et al., Nature (London) 314:377–380 (1985). The factors directing tissue-specific expression are not fully understood. The evidence from the work with the MMTV promoter and the mouse metallothionein promoter suggests that DNA sequences in 5'-flanking DNA are important. Stewart et al., Nucl. Acids Res. 12:3895–3906 (1984) and Palmiter and Brinster, Cell 41:343–345 (1985).

Clues to this problem are beginning to emerge from studies both in transgenic animals and in cell culture systems. It is apparent that specific enhancer sequences in 5' flanking DNA, sometimes located far upstream from the transcription start site, and sequences in or close to the promoter itself, are involved in tissue-specific gene expression. Gene expression in transgenic mice has been targeted to the appropriate tissue by inclusion of 5'-flanking and/or 3'-flanking DNA from the homologous gene in the case of $\beta$-globin, elastase, $\alpha$-fetoprotein, $\alpha$-A-crystalline and insulin. Magram et al., Nature (London) 315:338–340 (1985); Ornitz et al., Nature (London) 313:600–602 (1985); Krumlauf et al., Mol. Cell. Biol. 5:1639–1648 (1985); Overbeek et al., Proc. Natl. Acad. Sci. USA 82:7815–7819 (1985); and Hanahan, Nature (London) 315:115–121 (1985).

The insulin gene has been analyzed the most extensively. The rat insulin I gene requires both an enhancer region between −103 and −133 and the promoter region itself for expression of a marker gene in hamster insulinoma (HIT) cells compared to BHK cells. Edlund et al., Science 230:912–916, (1985). Furthermore, the rat insulin II gene requires a 530 bp 5'-flanking sequence to direct the expression of an SV40 oncogene to the $\beta$ cells of the pancreas in transgenic mice. Hanahan, Nature (London) 315:115–121 (1985).

The bacterial chloramphenicol acetyltransferase (CAT) gene expression has been targeted to the eye lenses by linking a −364 to +45 DNA fragment of the murine $\alpha$-A-crystalline to the coding sequence of the CAT gene. Overbeek et al., Proc. Natl. Acad. Sci. USA 82; 7815–7819 (1985).

The ability to target specific genes to the mammary gland should result in the efficient synthesis and secretion of proteins, ultimately impacting the fields of biotechnology, pharmacology, medicine, food science and cancer research. For example, while a variety of expression vectors have been developed for the efficient synthesis of proteins in bacteria and yeast, in many cases the biological activity of these proteins is impaired because of the failure to correctly process these proteins. Development of mammalian cell culture systems provides an alternative strategy but the cost of these cell cultures may be prohibitive. The mammary gland provides a highly efficient in vivo model for the synthesis and secretion of grams of protein per day. The secretion continues during the lactation cycles of a mammals' life. In addition, the mammary gland contains the necessary post-translational modification systems required for the clevage, phosphorylation and glycosylation of proteins. Therefore, using this approach should make it possible to efficiently synthesize and secrete biologically important molecules. For example, proteins, hormones, growth factors, drugs, lipids and carbohydrates can be synthesized and secreted, providing new tools in medicine and pharmacology. This methodology also provides a method to manipulate the composition of mammary fluid (milk) by altering its protein, carbohydrate and lipid composition and by the inclusion of bacteriostatic agents. These changes will represent important changes in agricultural and food technology science. Additionally, the ability to target oncogenes to the mammary gland will facilitate basic breast cancer research, because it provides a model to analyze the basic mechanisms of transformation in mammary epithelial cells. This investigational methodology is not available when using in vitro cell culture systems.

The present invention provides a method that not only targets the expression of genes in the mammary gland but also provides for efficiently secreting these proteins during lactation.

SUMMARY OF THE INVENTION

An object of the present invention is a recombinant DNA gene complex which directs the synthesis of biological active agents into milk.

An additional object of the present invention is the development of a transgenic mammal which secretes biological active agents in its mammary glands.

A further object of the present invention is the development of a transgenic mammal which secretes altered milk for use in pharmacology, medicine, cancer research, agriculture and food production.

Another object of the present invention is the development of a transgenic mammal which reproduces itself.

Thus, in accomplishing the foregoing objects there is provided in accordance with one aspect of the present invention the provision as a composition of matter, a recombinant DNA gene complex, comprising a promoter sequence, an enhancer sequence, a signal peptide sequence and a coding sequence derived from a gene coding for a biological active agent. The promoter sequence, enhancer sequence and signal peptide sequence derive from at least one mammary gland-specific gene and facilitate the expression of the coding sequence in the mammary gland. The coding sequence is selected from genes coding for biological active agents.

A further aspect of the present invention is the development of the above recombinant DNA gene complex, comprised further of a 5' untranslated mRNA sequence and a 3' untranslated mRNA sequence which are attached to the 5' and 3' ends respectively of the coding sequence. The 5' and 3' flanking sequences increase the stability of the messenger RNA synthesized by the recombinant DNA gene complex.

Another aspect of the present invention is the development as a composition of matter a transgenic mammal for synthesizing peptides in the mammary gland, comprising a germ line which includes a recombinant DNA gene complex; the germ line is transmittable to subsequent generations. Another aspect of the transgenic mammal is that it can be any mammal. The preferred embodiment is a non-human mammal.

A further aspect of the present invention is a method of targeting the synthesis of peptides of at least one specific gene to the mammary gland, comprising the step of, inserting a recombinant DNA gene complex into a germ line of a mammalian. Another embodiment includes a method for growing the embryo in an environment conducive to differentiation and development into a mammal. A further embodiment comprises the step of confirming the stable incorporation of the gene complex into the germ line. Another embodiment comprises the further step of testing the mammary tissue and milk from the mammal for the expression of the coding sequence. An additional embodiment comprises the step of establishing the proper functioning of the gene complex.

An additional aspect of the present invention is a method for constructing a mammary gland specific gene complex, comprising the steps of linking a promoter sequence, an enhancer sequence, and a signal peptide sequence selected from mammary gland-specific genes, and a coding sequence from a gene which codes for a biological active agent. One embodiment the method comprises the further step of linking a 5' untranslated mRNA and a 3' untranslated mRNA sequence.

There is provided in accordance with another aspect of the present invention a method of synthesizing a biologically active agent in mammary gland comprising of steps of constructing a recombinant DNA gene complex, inserting this gene complex into a germ line of a mammalian embryo, growing the embryo to maturity and testing milk produced by the mammal containing the gene complex for the biological active material.

A further aspect of the present invention is a method of preventing spoilage in milk comprising the step of inserting a recombinant DNA gene complex which includes a bacteriostatic coding sequence into the germ line of a mammalian embryo.

Another aspect of the present invention is a method of examining the mechanisms of mammary cancer comprising the steps of inserting a recombinant DNA gene complex which includes an oncogene into a germ line of a mammalian embryo and mechanisticly analyzing the resultant development of cancerous tissues.

Another aspect of this invention is the development as a composition of matter a strain of transgenic mammals which secrete customized milk. The customized milk can have altered concentrations of naturally occurring compounds and/or can contain foreign compounds. The foreign compounds can be drugs, hormones, peptides, proteins, lipids, carbohydrates and bacteriostatic agents. These foreign compounds are synthesized from genes derived from bacterial, animal and human genomes.

A further aspect of the present invention is a process for facilitating the production of dairy products comprising the step of incorporating customized milk into the production of the dairy products.

An additional aspect of the present invention is a food product including customized milk produced from a transgenic mammal.

Further objects, features and advantages will be apparent from the following description of preferred embodiments of the invention.

BRIEF DESCRIPTION OF THE DRAWINGS

FIG. 1A. A recombinant DNA gene complex. E represents the enhancer sequence; P represents the promoter sequence; signal peptide represents the tissue specific sequence; cDNA represents the specific gene to be synthesized; the narrow line (–) represents flanking sequences; and the thick line () represents intronic sequences.

FIG. 1B. An alternative recombinant DNA gene complex. The symbols are the same with the addition that 5'UT represents the 5' untranslated mRNA and 3'UT represents the 3' untranslated mRNA.

FIG. 2. Structure of the transferred rat β-casein gene. The diagram includes the entire gene with about 1.3 Kb 5' flanking DNA and 1 Kb λ DNA. This structure was isolated and subcloned from single phage clones by a Kpn I-BAM HI digestion. Also shown is the 1.9 kb Eco RI probe used to analyze the genomic DNA.

FIG. 7. RNase protection assay of mammary gland RNA from transgenic mice. RNA was extracted from lactating mammary tissue obtained as biopsy samples from three female $F_o$ mice. Expression of the rat β-casein transgene was detected in RNA using an RNase protection assay. The letters represent as follows: Lane A (probe alone), lane B (0.5 μg of rat lactating RNA), lane C (50 μg of lactating RNA from a noninjected control), Lanes D, E, and F (50 μg of RNA from positive transgenic mice) and lane G (50 μg of tRNA).

FIG. 8. Construction of casein-CAT fusion genes. The structure of the $pSV_oCAT$ expression sector. Four β-casein-CAT and one γ-casein-CAT fusion genes are shown containing up to 2.3 Kb of 5' flanking DNA and in some cases the 5' untranslated exon I and a portion of intron A of these genes. Numbering is relative to the casein mRNA CAP site designated as +1. The structural gene sequences are shown with exons in black and introns in white.

DETAILED DESCRIPTION OF PREFERRED EMBODIMENTS

Figure 3:
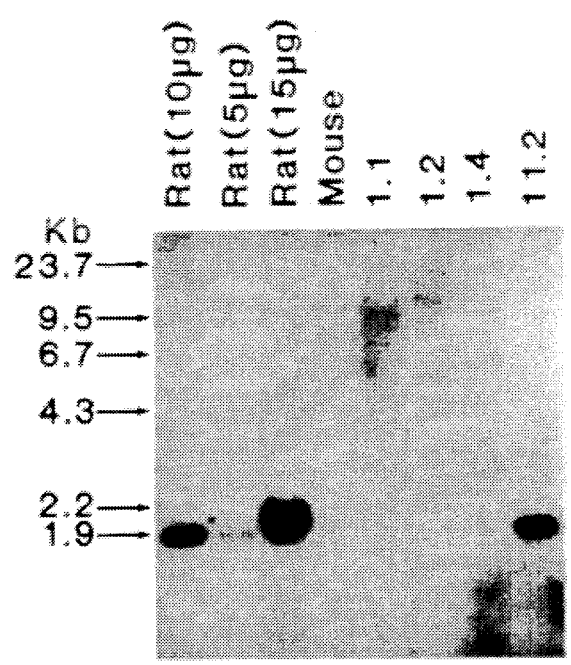
FIG. 3. Transfer of the Rat β-casein gene into transgenic mice. Analysis of the 1.9 Kb Kpn I-Bam HI fragment after insertion into mice embryos. The Rat and mouse DNA serve as controls.

One embodiment of the invention as a composition of matter is a recombinant DNA gene complex including a promoter, enhancer, signal peptide and coding sequences. In this combination the promoter, enhancer and signal peptide sequences are derived from mammary gland-specific genes and the coding sequence codes for a biological active agent. The usual method of constructing a mammary gland specific recombinant DNA gene complex includes the linking of a promoter, enhancer, signal peptide and coding sequence together. FIG. 1A displays one embodiment of the invention showing the linking of a gene promoter sequence (P) with its enhancer sequence (E) by flanking sequences. These sequences are derived from genes which normally are specifically expressed only in mammary tissue. For example, these sequences can be obtained from genes which code for α-casein, β-casein, γ-casein, κ-casein, α-lactalbumin, β-lactoglobulin, and whey acidic protein.

The promoter-enhancer complex is then linked to a signal peptide exon sequence. A variety of signal peptide exons which are specific to the mammary gland are available. The signal peptide exons play a role in the efficient translocation, recognition, removal and secretion of proteins into milk. Once the protein, carbohydrate, peptide or fat is secreted into the milk, standard separation procedure can be used to purify the components. Although the signal peptide will facilitate post-translational processing, the intrinsic characteristics of some synthesized molecules may prevent secretion into the milk. Thus, mammary tissue must be collected and the molecule of interest purified from the tissue. This approach is less satisfactory because the collection of mammary tissue prevents the continual production of the compound of interest and the separation of components from tissue is a more difficult procedure than separation from milk. Specific embodiments employ exons II of the α-, β-, and γ-casein genes and exon I of the whey acidic protein gene.

The coding region (cDNA) of the gene of interest is attached to the promoter-enhancer-signal peptide complex by an intron sequence. The coding region can be any gene or part a gene which codes for a molecule. It can include both intron and exon regions of the gene. For example, genes which code for proteins, milk proteins, lipids, carbohydrates, hormones, bacterial compounds (drugs, bacteriostatic agents), antibodies, antigens, and enzymes can be linked to the promotor-enhancer-signal complex.

In the preferred embodiment the coding sequence is selected from genes coding for biological active agents selected from the group consisting of α-casein, β-casein, γ-casein, κ-casein, α-lactalbumin, β-lactoglobulin, whey acidic protein, hormones, drugs, proteins, lipids, carbohydrates, growth factors, chloramphenicol acetyltransferase and bacteriostatic agents. In a preferred embodiment the mammary gland-specific gene is selected from the group consisting of the genes coding for α-casein, β-casein, γ-casein, κ-casein, α-lactalbumin, β-lactoglobulin and whey acidic protein.

Another embodiment uses the same gene in deriving the promoter sequence, enhancer sequence and signal peptide sequence. Other specific embodiments employ the promoter, enhancer and signal peptide sequences of the β-casein gene, and a coding sequence for either the β-casein gene or the chloramphenicol acetyltransferase gene.

An additional embodiment as a composition of matter is the recombinant DNA gene complex shown in FIG. 1B. This embodiment includes a 5'- untranslated sequence (5'UT) and a 3'-untranslated sequence (3' UT) of a messenger RNA (mRNA) linked to the coding region of the gene which is attached to the promotor-enhancer-signal complex. The untranslated mRNA sequences can be linked by introns. These untranslated mRNA sequences are transcribed and are attached to the mRNA. These untranslated regions aid in protecting the mRNA of the coding region from rapid breakdown. Naturally occurring genes whose mRNA shows a long half-life are good candidates for these untranslated regions. Examples of untranslated regions which may be utilized in these constructions include the untranslated mRNA sequences of the β-casein, β-globin and vitellogenin mRNA's. It has been found that the β-casein gene sequence provides a preferred embodiment.

The enhancer-promoter-signal peptide and enhancer-promoter-5' untranslated mRNA sequence—signal peptide 3' untranslated mRNA sequence constructs can be incorporated into a vector. Then the various cDNAs can be incorporated whenever needed. The cDNAs are like cassettes being inserted into a DNA sequence designed to specifically secrete compounds into milk. Thus a variety of recombinant DNA gene complexes can be easily formed.

Once the recombinant DNA gene complex (foreign gene complex) is made, with or without untranslated sequences, it is integrated into the genome (germ line) of the host mammal. The integration of the foreign gene complex into the germ line creates as a composition of matter, a transgenic animal. Furthermore, integration into the germ line allows the transmission of the foreign gene complex to offspring. Thus, a strain of mammals containing the foreign gene complex can be maintained. The foreign gene complex can be included into the genome of any mammal. In one preferred embodiment a non-human mammal is used.

The synthesis of biological active agents can be targeted to the mammary gland by inserting the recombinant DNA gene complex into the germ line of a mammalian embryo. An additional embodiment includes the step of inserting the embryo into an appropriate environment which is conducive to differentiate and develop the embryo into a mammal. After the mammal is born the additional step of genome screening can be done to establish that a stable incorporation of the foreign gene complex into the host genome has occurred. After the mammal reaches maturity, the lactating gland can be examined to confirm that mRNA and/or molecule synthesis of the foreign gene complex is occurring in the mammary gland. This step can be used to establish the proper functioning of the recombinant gene complex. Depending upon the characteristics of the foreign gene which is integrated, a variety of screening procedures are available. The screening procedure can include probe analysis, mRNA analysis, enzyme analysis, bacterial assays, antibody screens and protein, carbohydrate and lipid analysis.

In one preferred embodiment the foreign gone complex is inserted into the germ line of a mammal at the one cell stage of an oocyte. If the integration occurs at the one cell stage, a probe to the foreign gene complex can be utilized to test any tissue, but, if integration occurs at later stages in development the tissue to be examined is limited to those developing from the cell line where integration occurs. The injected oocyte is then inserted into the oviducts of a host animal with the same germ line.

Specific Examples of Foreign Gene Complexes

The 34.4 kb region of genomic DNA containing the 7.2 kb rat β-casein gene has been characterized. Jones et al J. Biol. Chem. 260:7042–7050 (1985) the disclosure of which is incorporated by reference. The entire gene and either 1.3 or 2.3 kb of 5'-flanking DNA were isolated and subcloned from single phage clones by either a Kpn I-Bam HI or Bam HI-Bam HI digestion. Jones et al. J Biol. Chem. 260:7042–7050 (1985). These constructions contain in addition 1 kb (KpmI-Bam HI) or 5 kb (Bam HI-Bam HI) of λ DNA. FIG. 2 shows the KpnI-BamHI digestion fragment containing the β-casein gene with 1 kb, 5' flanking DNA and 1 kb of λ DNA. Alternatively, a 14.6 kb Bam HI-Bam HI fragment free of prokaryotic DNA can be isolated by ligation of a Bam HI-Sal I fragment from phage B12 to a Sal I-Bam HI fragment from phage B99. This construction contains 7kb of 5'-flanking DNA, the entire gene and 400 bp of 3'-flanking sequence.

An example of a recombinant DNA gene complex includes a glucocorticoid response element (GRE) from mouse mammary tumor virus long terminal repeat. This is inserted 5' to the mammary specific enhancer sequence (FIG. 1A). Its addition is facilitated by the addition of appropriate restriction enzyme linkers. The GRE can be excised from plasmid pTK2A1 by digestion with Xho II to generate a 340 bp fragment capable of conferring glucocorticoid inducibility on the adjacent gene (Godowski et al., Nature 325: 365–368, (1987). The GRE permits an additional 10- to 20-fold induction of the adjacent gene due to the elevated glucocorticoid levels present during lactation.

One example of a recombinant DNA gene complex which can be used to elicit efficient tissue-specific expression in transgenic mice is the entire rat β-casein gene containing 7 kb of 5'-flanking DNA and lacking the procaryotic vector sequences. The large and complex nature of the casein genes, leaves few restriction enzyme sites available to excise the λ DNA sequences without cleaving the gene at multiple sites. Thus, removal of the λ sequences from the Kpn I-Bam HI fragment requires Bal 31 digestion followed by subcloning and DNA sequencing. Maniatis, et al., Molecular Cloning: A Laboratory Manual, Cold Spring Harbor Press pp. 207–209 (1982), the disclosure of which is incorporated by reference. Furthermore, the entire gene and its large flanking sequences can be important for tissue-specific regulation.

An additional recombinant DNA gene complex was formed using β-casein-CAT fusion genes. Bisbee and Rosen, ULCA Symposium on Molecular and Cellular Biology "Transcriptional Control" (1986), the disclosure of which is incorporated by reference. This construction contains up to 2.3 kb of 5'-flanking DNA. This can be conveniently excised from the vector DNA using unique Nde I and Bam HI sites. The linear fragment free of vector DNA is used. An alternative construction of the β-casein-CAT complex is the ligation of additional 5' flanking sequences to the Xba I linker used in the construction of the casein-CAT fusion genes. Only a few Xba I sites exist in the 7 kb of 5' flanking DNA therefore a Bam HI-Xba I (partial digestion) fragment is generated containing the missing upstream sequence. Another method of forming recombinant DNA gene complexes when tissue-specific enhancer sequences are present within the gene is to screen for the enhancer sequences by assaying the restriction endonuclease fragments spanning the gene and by cloning with appropriate linkers into a vector. In the case of CAT the vector is a $SV_1CAT$ vector. Gorman et al., Mol. Cell. Biol. 2:1044–1051 (1982), the disclosure of which is incorporated by reference. This vector contains a constitutive promoter from $SV_{40}$, but lacks the SV40 enhancer sequence. It is, therefore, useful for screening for promoter-independent enhancer activity in different DNA fragments. Furthermore, a β-casein-CAT construction containing only 511 bp of 5'-flanking DNA can be utilized. In the transgenic mice the unrearranged copies of the transferred genes, rat β-casein and CAT, are analyzed for expression.

In order to target expression to the mammary gland and to efficiently secrete these proteins during lactation a signal peptide must be linked to the complex. One example is the linkage of the 63 bp casein signal peptide exon sequence in phase to CAT. The signal peptide for casein has been shown to be highly conserved throughout mammalian evolution. Yu-Lee et al., 14:1883–1902 (1986), the disclosure of which is incorporated by reference. Although other signal peptides discussed above are available it is advantageous to use a highly conserved sequence to facilitate efficient secretion in the mammary gland. Transfection of DNA encoding foreign secretory proteins into regulated secretory cells has shown the specificity of protein sorting into secretory vesicles. Kelly, Science 230:25–32 (1985) the disclosure of which is incorporated by reference. For example, a HindIII fragment containing the second exon (exon II) of the β-casein gene can be isolated. The HindIII sites are 14 bp 3' to the +2 amino acid of the mature casein and 548 bp 5' to the start of exon II, Jones et al., J. Biol. Chem. 260:7042–7050 (1985). To delete the termination codon in phase with the ATG 3' to the +2 amino acid, Bal 31 digestion is performed and HindIII linkers are inserted. This fragment is inserted in the HindIII site of an $SV_2CAT$ vector Gorman et al., Mol. Cell. Biol. 2:1044–1051 (1982) and Rosen et al., In: Membrane Receptors and Cellular Regulation Alan R. Liss, New York pp 385–396 (1985) the disclosure of which is incorporated by reference.

An alternative approach is to synthesize directly a 45 bp oligonucleotide containing unique restriction enzyme linkers. This can be ligated directly to the Hind III site in the β-casein-CAT vector. The oligonucleotide approach is preferred since the cleavage sequences can be controlled for better efficiency and precision.

The vector which is constructed or synthesized is transfected into COMMA-ID cells, and CAT is efficiently expressed. Bisbee and Rosen ULCA Symposium on Molecular and Cellular Biology, "Transcriptional Control" (1986). This construction results in a CAT fusion protein containing an additional 14 amino acids fused to the amino terminus of CAT following cleavage of the signal peptide sequence.

In another preferred embodiment the previously determined cis-acting regulatory sequences required to elicit tissue-specific expression to the casein signal peptide-CAT construction are linked to the above example constructions. This is accomplished either by deleting the SV40 72 bp enhancer from the above construction using Acc I and Sph I (this generates essentially the $SV_1CAT$ vector) and inserting a mammary specific enhancer fragment, or by using partial HindIII digestion at an upstream HindIII site at −330 bp to generate a fragment containing both the casein-specific promoter, exon I, intron A and exon II. In either case a linear DNA fragment lacking procaryotic vector sequences is used to generate transgenic mice.

CAT activity can be determined by a variety of methods including enzymatic analyses in the medium (milk), cytoplasmic and tissue extracts and by immunological assays employing a dot blot method.

The casein signal peptide sequence may not be sufficient to target the secretion of all proteins, especially since secretion is dependent on many factors for example intrinsic hydrophobicity. Thus, other signal peptides or alterations to the flanking regions may be necessary to obtain secretion. The intrinsic signal peptide of a normally secreted protein such as growth hormone or tissue plasminogen activator could be included instead of the casein signal peptide. Alternatively the carboxy-terminal amino acids involved in anchoring the protein in the membrane may have to be deleted.

The authenticity of the example constructions can be confirmed by both restriction enzyme mapping and DNA sequencing.

Generation of Transgenic Mammals

Transgenic mammals can be generated by the process of incorporating foreign DNA sequences into the host genome. This process consists of embryo collection, injection of the DNA into the embryos, transfer of the surviving embryos to surrogate mothers, and screening the offspring for integration and expression of the exogenous gene. Transgenic mammals can include bacterial genes inserted into mammals to produce drugs, human genes inserted into non-human mammals to produce gram quantities of biological compounds in milk, human growth hormones incorporated into dairy animals, rat DNA incorporated into mouse, rat or bovine DNA incorporated into dairy animals, and DNA encoding goat sheep or pig milk proteins inserted into bovine.

Specific embodiments have included a method of preventing spoilage in milk by the insertion of a recombinant DNA gene complex into a germ line of a mammalian embryo. In the preferred embodiment the coding sequence for a bacteriostatic agent is inserted. Additional embodiments include the insertion of a recombinant DNA gene complex including an oncogene into the germ line of a mammalian embryo. The resultant transgenic mammal can be examined and the mechanism of the development of cancerous tissues can be analyzed. This process also provided a procedure for facilitating the production of dairy products by incorporating customized milk into the production. The customized milk is produced in a transgenic mammal. The customized milk can include biological active agents and can be used to produce a variety of products including food, drugs, cosmetics, hormones, carbohydrates, fats, amino acids and proteins.

Specific example of rat β-casein integration into mice.

1. Embryo collection

One cell embryos are collected by flushing the oviducts of female mice which have been administered a superovulatory regime of gonadotropins. The gonadotropin regime is strain-dependent but essentially consists of intraperitoneal (i.p.) injection of pregnant mare serum gonadotropin (PMS) followed by a later injection of human chronic gonadotropin (hCG) i.p. After the final gonadotropic administration, the female mouse is mated to a male mouse. The females are sacrificed approximately 18–20 hrs after hCG administration the oviducts are flushed and the one cell embryos are made ready for injection.

In one specific embodiment approximately 14–18 g ICR females are injected with approximately 5 I.U. PMS followed about 48 hours later by approximately 5 I.U. injection hCG. Young immature mice respond better to superovulation than older animals. Though either can be used. A male B6 mousse is used in the mating.

2. Embryo injection

Embryos are placed in a drop of medium, Quinn, J. Reprod. Fert. 66:161–168 (1982) the disclosure of which is incorporated by reference, and supplemented with 5 µg/ml cytochalasin B. The drop of medium is covered with paraffin oil and the embryos are viewed with an inverted microscope using Hoffman optics. Injection of rat β-casein gene complex is accomplished by positioning the one cell embryo with a holding micropipette and injecting the rat β-casein gene complex into the male pronucleus with a finely pulled injection micropipette. The control of the fluid flow through the micropipettes consists of connecting Stoelting micrometer syringes to the micropipettes with Teflon tubing. The entire system is filled with paraffin oil allowing positive pressure for injection and negative pressure for holding the embryo to be injected under fine control.

The rat β-casein gene complex to be injected is dissolved in a solution of 10 mM Tris, pH 7.5, and 0.25 mM EDTA at a concentration of about 2 ng/µl. Brinster et al., Proc. Natl. Acad. Sci. USA 82:4438–4442 (1985) the disclosure of which is incorporated by reference. Approximately 1–2 pl of the β-casein gene complex solution is injected into the pronucleus. Embryo survival after injection is judged by the appearance of normal morphology.

3. Embryo transfer

The embryos surviving microinjection are placed in HT6 medium in preparation for transfer to the oviducts of 6- to 8-week old female mice. The recipient is administered PMS i.p. followed later by hCG and placed with a vasectomized male mouse. To aid the recipient in accepting the microinjection embryos the gonadotropic administration and mating coincide with the schedule of the donor mouse.

In one example about 20–22g ICR females were injected with about 2 I.U. PMS j.p. followed about 48 hours later with 2 I.U. hCG i.p. Those females with vaginal plugs after being placed with vasectomized males were used as recipients.

The recipient females are anesthetized, the oviducts are exposed with dorsolateral incision and the embryos are placed through the fimbrae of the oviduct with the use of a finely-pulled Pasteur pipette. The oviducts are returned to the peritoneal cavity and the wound is closed.

The success of the embryo transfer is judged by the birth of mice about 19–21 days after transfer. Success of the microinjection is assessed by Southern hybridization analysis of DNA isolated from mouse tail biopsies.

Specific example of bacterial CAT integration into mice.

1. Embryo collection - same procedures as under rat β-casein example.

2. Embryo injection

The same procedures as employed under the rat p-casein example are used except that the bacterial CAT gene complex is injected into the male pronucleus of the one cell embryo. The bacterial CAT gene complex to be injected is dissolved in a solution of 10 mM Tris, pH 7.5, and 0.25 mM EDTA as a concentration of about 2 ng/ul. Approximately 1-2 pl of the bacterial CAT gene complex solution is injected into the pronucleus. Embryo survival after injection is judged by the appearance of normal morphology.

3. Embryo transfer

The same procedures employed for the β-casein gene complex are employed. The success of the embryo transfer is judged by the birth of mice about 19-21 days after transfer. Success of the microinjection of the bacterial CAT is assessed by Southern hybridization analysis of DNA isolated from mouse tail biopsies.

Specific example recombinant DNA gene complex integration into cattle, sheep and pig embryos The embryo collection and injection procedures are as previously described. Hammer et al. Nature (London) 315:343-345 (1985), and Kraemer et al In: Gene Transfer in Cattle and Sheep Banbury Report Nov. 20 pp. 221-227 (1985) the. disclosure of which is incorporated by reference. The major difference between mice and cattle, sheep and pigs is in the visualization of the pronuclei, in cattle, sheep and pigs the oocytes are not clear. Visualization is facilitated by centrifugation at about 15,000 g for approximately 3 minutes. This centrifugation procedure stratifies the cytoplasm and leaves the pronuclei and nuclei visible by interference contrast microscopy.

Analysis of Transferred Gene Structure and Expression

1. Isolation of DNA

A small tissue sample is homogenized with a Brinkman polytron in SET buffer (150 mM NaCl, 20 mM Tris, pH 7.8, 1 mM $Na_2$ EDTA) at 37° C. overnight and extracted with phenol, phenol/chloroform/isoamyl alcohol, and chloroform/isoamyl alcohol. The DNA is recovered by ethanol precipitation or spooling. The concentration of DNA is determined by the specific fluorescence assay. Labarca and Paigen, Anal. Biochem. 102:344-352 (1980) the disclosure of which is incorporated by reference. In mice about 1-2 cm of tail can be cut off and analyzed.

2. Southern and DNA dot blot assays

Initially the putative transgenic animal is screened for the presence of the transferred gene by Southern blotting. Ten μg of genomic DNA from control organisms supplying foreign DNA, control host and transfer host are digested with restriction endonuclease, separated by agarose gel electrophoresis, transferred to nitrocellulose, and hybridized with a unique gene probe.

For example when the rat β-casein gene is incorporated into mice a 1.9 kb EcoRI gene probe is used. The status of the β-casein integration is analyzed by digesting DNA with other restriction endonucleases, for example, Kpn I and Bam HI, and probed with the 1.9 kb fragment as well as with a 2.8 kb 5'-EcoRI fragment. The copy number of the transferred gene can be determined by a DNA dot blot assay using rat genomic DNA standards (FIG. 3). Kafatos et al., Nucl. Acid Res. 7:1541-1553 (1979) the disclosure of which is incorporated by reference.

3. Mammary Gland Biopsy, RNA Isolation and Northern Blot

Lactating mammals are anesthetized and a biopsy of mammary gland tissue is removed and subjected to RNA extraction using the guanidine thiocyanate-CsCl method. Chirgwin et al., Biochemistry 18:5294-5299 (1979) the disclosure of which is incorporated by reference. Mammary gland RNAs from biopsy samples and control tissues are separated by glyoxyai-agarose gel electrophoresis, transferred to nitrocellulose or nylon membranes and hybridized with a cRNA riboprobe. Zinn et al., Cell 34:865-879 (1983) the disclosure of which is incorporated by reference.

For example, transgenic mice were anesthetized and the fourth mammary gland was removed and subjected to RNA extraction. The rat β-casein gene mRNA was detected on nitrocellulose by hybridization with a rat 3'-cRNA riboprobe (FIG. 7).

4. RNase and S1 Nuclease Mapping

Correct initiation and termination of the transferred foreign gene complex can be determined by RNase and S1 nuclease mapping, respectively.

For example, in rat β-casein gene RNase mapping, an 800 bp riboprobe which covers the 5' flanking, the first exon, and a portion of intron A, is hybridized with RNA samples according to Zinn et al., Cell 34:865-879 (1983) and subjected to RNase A and RNase T1 digestion. The protected fragment is analyzed on an 8% polyacrylamide/urea sequencing gel.

Figure 5:
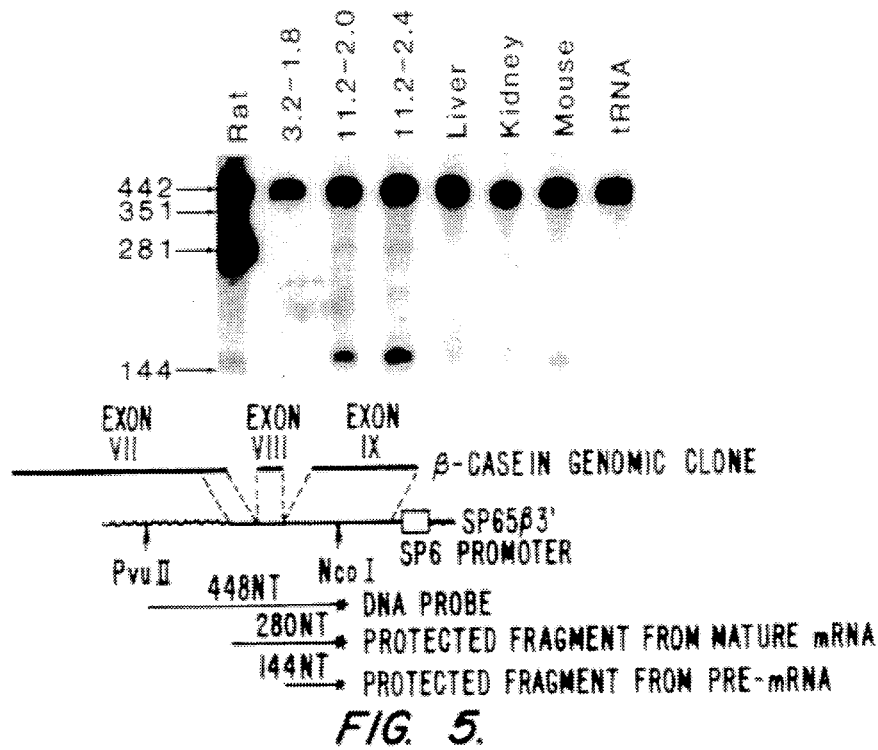
FIG. 5. Expression of the β-casein gene in transgenic mice. Results of RNA blots on RNA isolates from liver, brain, kidney. A specific S1 nuclease protection assay using the 3' noncoding region of the rat β-casein mRNA was used to distinguish rat and mouse mRNA's.

For example, in rat β-casein gene S1 nuclease mapping, two different probes are used (FIG. 5). The first probe is Pvu II-Nco I fragment labeled at the 3' end by polynucleotide kinase. The second probe is an Nco I-EcoRI genomic fragment which covers the 3' end of exon IX labeled at the 3' end by the Klenow fragment of DNA polymerase I. RNAs are hybridized with these probes, digested with S1 nuclease, and analyzed on a 5% polyacrylamide/urea gel. Maniatis, et al., Molecular Cloning: A Laboratory Manual, pp. 207-209 (1982). Each foreign gene which is incorporated will require its specific probe.

(e) CAT enzymetic and immunological assays

CAT enzymatic activity is assayed by the conversion of $^{14}$C-chloramphenicol to its acetylated derivatives. Gorman et al., Mol. Cell. Biol. 2:1044-1051 (1982). The results can be expressed as a function of the DNA or protein content of the cells or tissue studied, and in some cases per copy number of the integrated CAT gene determined by a DNA dot blot assay. CAT activity in milk is expressed per mg of protein. Alternatively CAT protein can be assayed using polyclonal or monoclonal antibodies and a Western dot blot procedure. One skilled in the art will recognize that other assays which detect either the protein or its activity are available. The assay of CAT secretion in cell culture is performed using early passage COMMA-ID cells grown on a floating type I collagen gel in about 5% fetal bovine serum containing insulin (approximately 5 μg/ml), hydrocortisone (approximately 1 μg/ml) and prolactin (approximately 1 μg/ml) for about 72 hrs following detachment of the gel. Under these conditions, β-casein mRNA represents approximately 5-10% of the level observed in lactating tissue. Rosen et al., Annals N.Y. Acad. Sci. 478:63-76 (1986) the disclosure of which is incorporated by reference. Under comparable conditions casein is efficiently secreted from primary mouse mammary cells grown on a floating collagen gel. Lee et al., Proc. Natl. Acad. Sci USA 82:1419–1423 (1985) the disclosure of which is incorporated by reference.

Analysis of Rat β-Casein incorporatin into mice

The principal difficulty with the analysis of the β-casein constructions is the lack of a clonal cell line, which displays hormonally-regulated casein gene expression. Casein gene expression in primary cell cultures is dependent on cell-cell, as well as cell-substratum interactions. Levine and Stockdale J. Cell. Biol. 100:1415 (1985) and Lee et al., Proc. Natl. Acad. Siv. USA 82:1419–1423 (1985). While both casein and whey acidic protein (wap)gene expression can be regulated by hormones in a serum-free medium in explant cultures, WAP gene expression is not observed in primary cultures or cell lines regardless of the culture conditions employed. Hobbs et al., J. Biol. Chem. 257: 3598–3605. Thus, transgenic mice provide an alternative in vivo system in which to analyze the functional role of cis-acting DNA sequences in the mammary gland.

Figure 4:
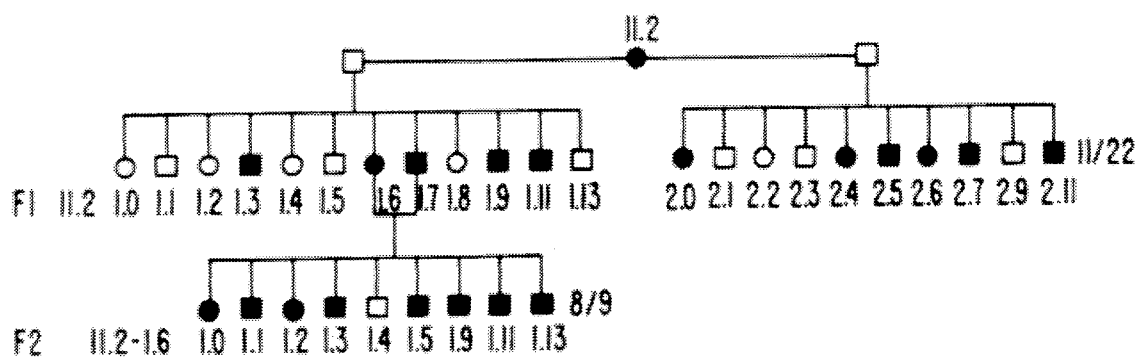
FIG. 4. Limited pedigree of Rat β-casein gene in transgenic mouse 11.2. Circles represent females and squares represent males. The filled-in symbols indicate mice containing the rat β-casein gene. DNA blots of tail samples were performed on $F_1$ and $F_2$ generation mice.

Using the Kpn I-Bam HI fragment several transgenic mice have been generated (FIGS. 2 and 3). The transmission and expression of the rat β-casein gene has been analyzed with a 1.9 kb Eco RI probe on genomic DNA blots. The specificity of the probe is shown by the observation that only weak cross-hybridization between the rat probe and a 10 kb mouse DNA Eco RI fragment is seen. Three different concentrations of rat genomic DNA, a sample of mouse DNA and four DNAs isolated from different $F_O$ mice are shown in FIG. 3. One mouse 11.2 contained the expected 1.9 kb fragment. More detailed analysis showed that approximately 4 copies of the entire, unrearranged Kpn I-Bam HI fragment was present in mouse 11.2. The transmission of the integrated rat β-casein gene was analyzed by performing tail blots on a series of $F_1$ and $F_2$ mice as summarized in FIG. 4. Of the $F_1$ generation, 11 of 22 inherited the gene with an unaltered copy number suggesting a single site of integration. Two of the positive $F_1$ mice were bred in order to establish a homozygous line. Of the $F_2$ generation, 8 of 9 were positive and data suggests that some of these mice may be homozygous.

Mammary gland biopsies have been performed from lactating mice. Mouse 11.2-2.4 was sacrificed and other tissues analyzed for casein gene expression as well. Initially, RNA blots were performed using an SP6 riboprobe synthesized from the 3' noncoding region of the rat β-casein mRNA. Expression of the correctly-sized mRNA (1.1 kb) was observed on RNA blots in lactating RNA isolated from mice 11.2-2.0 and –2.4. No expression was detected in RNA isolated from liver and brain, and barely detectable signal was seen in RNA isolated from kidney. Since the rat and mouse β-casein mRNAs are identical in size, a specific S1 nuclease protection assay was developed using the 3' noncoding region of the rat β-casein mRNA. This probe was used to establish that the expression of the β-casein mRNA that was detected was due to the transferred rat gene and not the endogenous mouse gene.

A strand separated 448 NI probe was prepared, which had been labeled at a unique Nco I site. Protection from the mature mRNA yields a fragment of 280 NT. If the pre-mRNA is not processed, a 144 NT fragment is generated. As shown in FIG. 5, 1 μg of RNA from lactating rat mammary gland gives a major band at 280 NT with a minor signal at 144 NT. A discrete signal of 280 NT is also seen in two of the transgenic mice (11.2-2.0 and –2.4), with a more intense band seen at 144 NT. Fifty μg of each RNA was assayed. No signals are seen in lactating RNA isolated from either a control or negative transgenic mouse, or using tRNA in the assay. Upon longer exposure a faint signal of 280 NT was also observed in the RNA extracted from kidney, but not from liver. These results show that the transferred rat β-casein gene was selectively expressed in the lactating mammary gland, but at a much lower level than the endogenous mouse gene. RNase and S1 protection experiments are used to determine if the rat β-casein gene transcripts are correctly initiated and processed.

Figure 6:
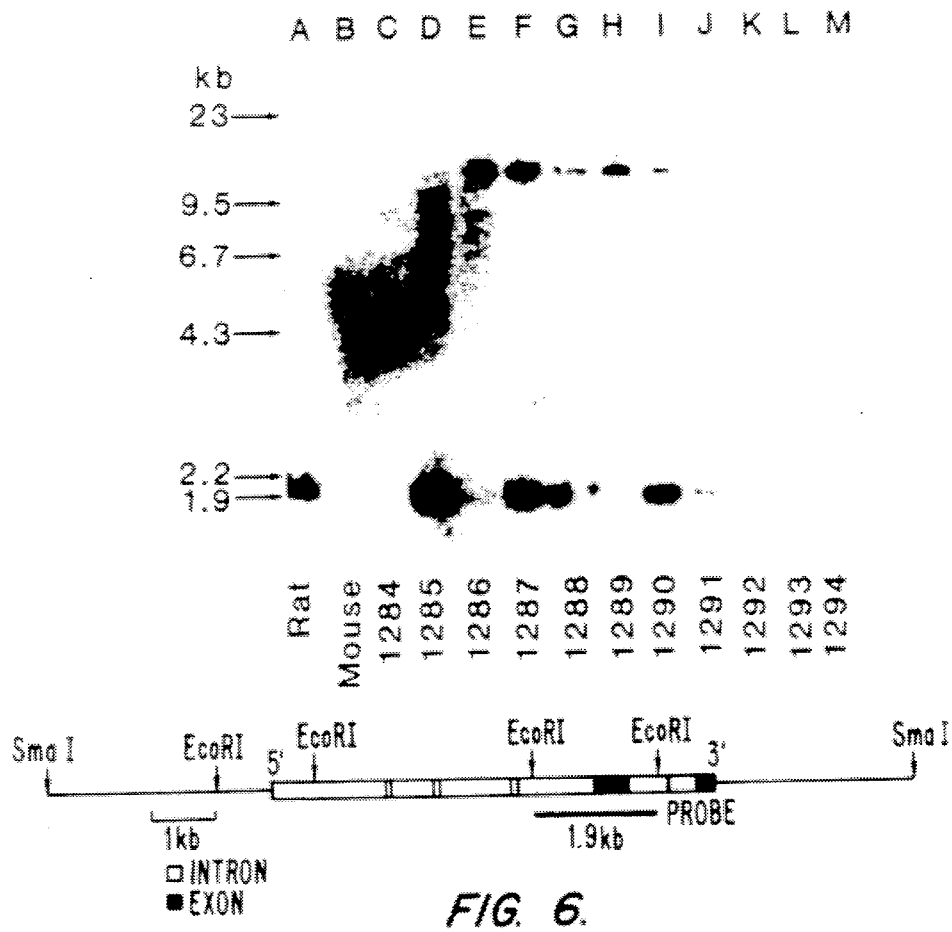
FIG. 6. Transfer of the Rat β-casein gene into transgenic mice. A genomic clone containing the entire rat β-casein gene and 3.5 Kb of 5' and 3.0 Kb of 3' flanking DNA was inserted into mouse embryos. Five mice show various numbers of copies of the transgene.

Because of the reported inhibitory effects of prokaryotic vector sequences on the level of tissue-specific transgene expression, and the possibility of enhancer sequences located further 5' or 3' to the gene, a genomic clone, free of vector sequences, containing the entire rat β-casein gene with 3.5 kb of 5' and 3.0 kb of 3' flanking DNA was isolated and used to generate transgenic mice. As illustrated in FIG. 6, the expected 1.9 kb EcoRI DNA fragment is shown in five mice (3 additional positive mice are not shown). RNA was extracted from lactating mammary gland biopsies of three female $F_o$ mice and casein gene expression analyzed as shown in FIG. 7 using a specific RNase protection assay. One of the three mice expressed the rat β-casein transgene (FIG. 7, lane F). This mouse showed the expected 450 NT protected fragment that was also observed in the control rat lactating RNA sample (FIG. 7, lane B). Examination of $F_1$ generation has shown that 7 of the 8 $F_o$ transgenic females transmitted the foreign gene complex to their offspring.

These results demonstrate the transfer and expression of the rat β-casein gene in transgenic mice. The levels of expression can be increased by the addition of 5' and/or 3' sequences to elicit efficient tissue-specific gene expression. Even though the conservation of 5' flanking sequences was observed in the first few hundred bp upstream of the CAP site, this does not preclude other sequences outside of this region from having an important role in tissue-specific expression and regulation. While this is not the case in the majority of genes, a sequence 5–7 kb upstream of the mouse α-fetoprotein gene has been observed to be necessary for efficient tissue-specific expression in transgenic mice. Hammer et al Science 235:53–58 (1987)

Analysis of CAT Incorporation

The $pSV_OCAT$ expression vector contains the gene encoding the bacterial enzyme chloramphenicol acetyltransferase. Promotion or enhancement of gene expression by specific gene sequences can be readily assayed by measuring CAT activity, a very sensitive enzymatic test that has no background in eukaryotic cells. A series of β- and γ-casein-CAT fusion genes have been constructed (FIG. 8). These have been assayed in a variety of mammary cell lines and primary cell cultures for hormonally-regulated promoter activity. Bisbee and Rosen, UCLA Symposium on Molecular and Cellular Biology "Transcriptional Control" (1986). The use of casein-CAT fusion genes in transgenic animals provides a rapid and sensitive assay for tissue-specific promoter and enhancer function.

One skilled in the art will recognize other uses of the foreign gene complex system for the secretion of proteins in the mammary gland and milk. While presently preferred embodiments and examples of the invention have been given for the purposes of disclosure, changes therein and other uses will occur to those skilled in the art which are encompassed within the spirit of the invention or defined by the scope of the appended claims.

What is claimed is:

1. A recombinant DNA complex to provide preferential mammary gland expression and secretion of a selected polypeptide comprising:
   (a) a casein promoter;
   (b) a transcribable DNA segment coding for said selected polypeptide, wherein said promoter does not naturally control the transcription of said DNA segment;
   (c) secretory DNA encoding a signal peptide functional in mammary secretory cells operably linked between said promoter and said DNA segment to facilitate secretion of said selected polypeptide;
   (d) a casein enhancer sequence capable of conferring enhanced preferential transcription of said recombinant DNA complex in mammary secretory cells when said complex is integrated into the genome of a non-human mammal, and
   (e) an intronic sequence from a casein gene or said transcribable DNA segment.

2. The recombinant DNA complex of claim 1 wherein said promoter is from a casein gene selected from the group consisting of α-casein, β-casein, γ-casein and κ-casein.

3. The recombinant DNA complex of claim 2 wherein said promoter comprises the promoter from a β-casein gene.

4. The recombinant DNA complex of claim 3 wherein said casein enhancer is selected from the group consisting of α-casein, β-casein, γ-casein and κ-casein enhancers.

5. The recombinant DNA complex of claim 1 further comprising a mouse mammary tumor virus glucocorticoid response element.

6. The recombinant DNA complex of claim 1 wherein said secretory DNA encodes a signal peptide from a mammary gland specific gene.

7. The recombinant DNA complex of claim 6 wherein said mammary gland specific gene is selected from the group consisting of whey acid protein and casein genes.

8. The recombinant DNA complex of claim 7 wherein said mammary gland specific gene is a casein gene.

9. The recombinant DNA complex of claim 8 wherein said casein gene is selected from the group consisting of α-casein, β-casein, and κ-casein genes.

10. The recombinant DNA complex of claim 1 wherein said transcribable DNA segment encodes a normally secreted polypeptide and said secretory DNA encodes the signal sequence of said secreted polypeptide.

11. The recombinant DNA complex of claim 1 further comprising:
    (f) DNA encoding a 5' untranslated sequence from a mammary gland specific gene.

12. The recombinant DNA complex of claim 11 further comprising:
    (g) DNA encoding a 3' untranslated sequence.

13. The recombinant DNA complex of claim 1, wherein said intronic sequence links said transcribable DNA segment to said promoter.

14. The recombinant DNA complex of claim 1, wherein said intronic sequence is located within said transcribable DNA segment.

15. The recombinant DNA complex of claim 13, wherein said intronic sequence is a portion of an intron located between exons I and II of a rat β-casein gene.

16. A vector to provide preferential mammary gland expression and secretion of a selected polypeptide comprising:
    (a) a casein promoter;
    (b) a transcribable DNA segment coding for said selected polypeptide, wherein said promoter does not naturally control the transcription of said DNA segment; and
    (c) secretory DNA encoding a signal peptide functional in mammary secretory cells operably linked between said promoter and said DNA segment to facilitate secretion of said selected polypeptide,
    (d) a casein enhancer sequence capable of conferring enhanced preferential transcription of said recombinant DNA complex in mammary secretory cells when said complex is integrated into the genome of a non-human mammal, and
    (e) an intron from a casein gene.

17. A recombinant DNA complex to provide preferential mammary gland expression and secretion of a selected polypeptide comprising:
    (a) a casein promoter;
    (b) a transcribable DNA segment coding for said selected polypeptide, wherein said promoter does not naturally control the transcription of said DNA segment; and
    (c) secretory DNA encoding a signal peptide functional in mammary secretory cells operably linked between said promoter and said DNA segment to facilitate secretion of said selected polypeptide,
    (d) a casein enhancer sequence capable of conferring enhanced preferential transcription of said recombinant DNA complex in mammary secretory cells when said complex is integrated into the genome of a non-human mammal,
    (e) an intron from a casein gene; and
    (f) a restriction enzyme linker sequence.

18. A recombinant DNA complex to provide preferential mammary gland expression and secretion of a selected polypeptide comprising:
    (a) a casein promoter;
    (b) a transcribable DNA segment coding for said selected polypeptide, wherein said promoter does not naturally control the transcription of said DNA segment; and
    (c) secretory DNA encoding a signal peptide functional in mammary secretory cells operably linked between said promoter and said DNA segment to facilitate secretion of said selected polypeptide,
    (d) a casein enhancer sequence capable of conferring enhanced preferential transcription of said recombinant DNA complex in mammary secretory cells when said complex is integrated into the genome of a non-human mammal, and
    (e) an intron from a casein gene;
    wherein the recombinant DNA complex is linear.

* * * * *